United States Patent [19]

Surmatis et al.

[11] 3,941,841
[45] Mar. 2, 1976

[54] METHOD FOR SYNTHESIZING RHODOXANTHIN

[75] Inventors: Joseph Donald Surmatis; Armin Walser, both of West Caldwell, N.J.

[73] Assignee: Hoffmann-La Roche Inc., Nutley, N.J.

[22] Filed: May 17, 1974

[21] Appl. No.: 471,089

Related U.S. Application Data

[62] Division of Ser. Nos. 153,090, June 14, 1971, Pat. No. 3,830,844, and Ser. No. 826,022, May 19, 1969, Pat. No. 3,624,105, which is a division of Ser. No. 617,827, Feb. 23, 1967, Pat. No. 3,466,331.

[52] U.S. Cl............................................ 260/586 R
[51] Int. Cl.² ........................................ C07C 49/48
[58] Field of Search.......... 260/586 R, 586 P, 586 C

[56] References Cited
UNITED STATES PATENTS

| | | | |
|---|---|---|---|
| 2,819,297 | 1/1958 | Isler et al. | 260/586 R |
| 2,827,481 | 3/1958 | Isler et al. | 260/586 C |
| 2,827,482 | 3/1958 | Isler et al. | 260/586 R |
| 3,354,218 | 11/1967 | Surmatis | 260/586 P |

*Primary Examiner*—Norman Morgenstern
*Attorney, Agent, or Firm*—Samuel L. Welt; Jon S. Saxe; Richard A. Gaither

[57] ABSTRACT

A method by which rhodoxanthin can be synthesized from 3-ethylenedioxy-β-ionone as well as new and novel intermediates produced in the synthesis. Rhodoxanthin is a well-known coloring agent for foodstuffs, including beverages, pharmaceutical and cosmetic preparations.

1 Claim, No Drawings

METHOD FOR SYNTHESIZING RHODOXANTHIN

CROSS REFERENCE TO RELATED APPLICATIONS

This is a division, of application Ser. No. 153,090 filed June 14, 1971 now U.S. Pat. No. 3,830,844.

This application is a divisional application of U.S. Pat. application Ser. No. 826,022 filed May 19, 1969, now U.S. Pat. No. 3,624,105 which in turn is a divisional application of Ser. No. 617,827 filed Feb. 23, 1967, now U.S. Pat. No. 3,466,331.

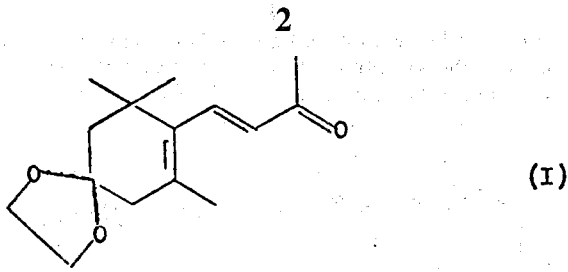

Rhodoxanthin which has the formula:

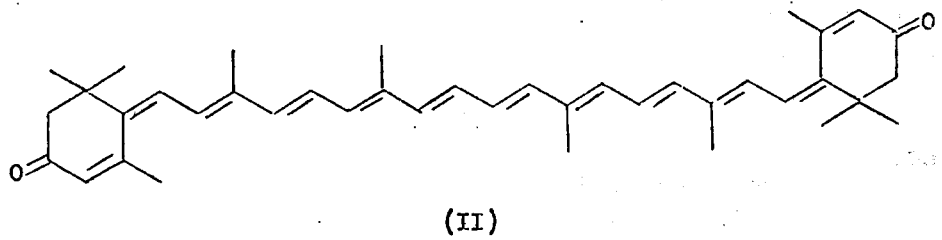

BACKGROUND OF THE INVENTION

This invention is directed to a method whereby rhodoxanthin can be synthetically produced without the necessity for isolating rhodoxanthin or its intermediates from their natural source.

Rhodoxanthin, which is formed in nature in the berries of evergreen trees such as Paxus Baccata, is widely used as a coloring material for foodstuffs and beverages as well as pharmaceutical and cosmetic preparations. Rhodoxanthin imparts to foodstuffs, pharmaceutical and cosmetic preparations a red coloration. In the past rhodoxanthin has been produced by isolating this material from its natural source such as from the berries of evergreen plants. This procedure has proven extremely disadvantageous due to the fact that rhodoxanthin occurs only in small amounts in these berries. Therefore, a great quantity of these berries must be utilized in order to isolate a small amount of rhodoxanthin. Additionally, the process whereby rhodoxanthin is isolated from the berries of green plants has proven extremely cumbersome and uneconomical. Up until the present time there has been no procedure for directly chemically synthesizing rhodoxanthin without isolating rhodoxanthin or precursors of rhodoxanthin from their natural source. Therefore, it has long been desired in the art to provide a method for chemically synthesizing rhodoxanthin so as to eliminate the necessity of isolating rhodoxanthin or its precursors from its natural source.

SUMMARY OF THE INVENTION

This invention relates to the synthesis of rhodoxanthin from can be synthesized from the compound of Formula I above through the preparation of a phosphonium salt intermediate of the formula

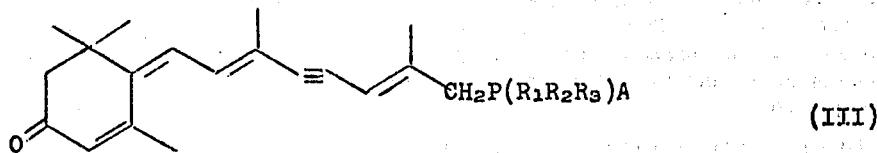

wherein $R_1$, $R_2$ and $R_3$ are straight and branched chain lower alkyl groups having from 1 to 7 carbon atoms; or aryl radical such as phenyl, naphthyl, etc.; or an aralkyl radical having from 7 to 15 carbon atoms such as benzyl; and A is an anion of a mineral acid, e.g., $Cl^-$, $Br^-$, $I^-$, $HSO_4^-$, etc. and an oxo aldehyde intermediate of the formula:

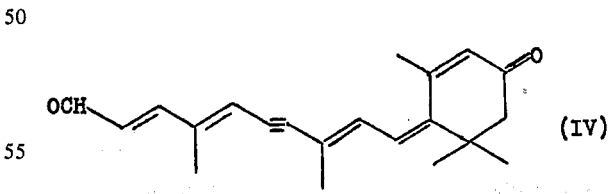

In accordance with this invention, the intermediates of Formulae III and IV above are reacted in the presence of a strong alkali and the reaction product is selectively reduced and hydrogenated at the triple bond to form rhodoxanthin.

In accordance with another embodiment of this invention, rhodoxanthin can be synthesized by the condensation of an intermediate of the formula:

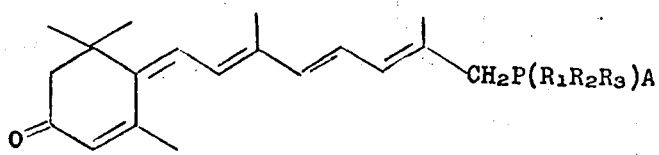

(V)

wherein $R_1$, $R_2$, $R_3$ and A are as above with an intermediate of the formula:

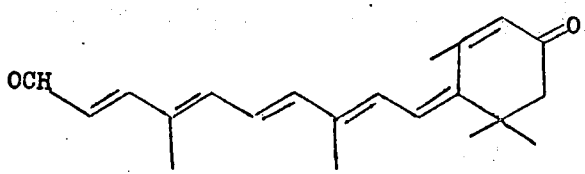

(VI)

in the presence of an inert organic solvent.

By means of the above processes of this invention, rhodoxanthin can be chemically synthesized simply and economically without the necessity for isolating the rhodoxanthin from its natural source.

The term "lower alkyl" as used throughout the specification denotes an alkyl radical containing from 1 to 7 carbon atoms such as methyl, ethyl, butyl, propyl, isopropyl, etc.

DETAILED DESCRIPTION OF THE INVENTION

The phosphonium salt compound of Formula III above is reacted in accordance with this invention with the oxo aldehyde compound of Formula IV to produce an acetylenic dioxo compound of Formula VII:

within lithium, sodium, potassium, rubidium, cesium, and francium are the preferred metallo moieties and wherein the preferred alkyl moieties are the lower alkyl groups and the preferred aryl moieties are phenyl and lower alkylsubstituted phenyl groups, with phenyl lithium and butyl lithium being the preferred metallo organics. In carrying out this reaction, temperature and pressure are not critical and this reaction can be carried out at room temperature and elevated or reduced pressure. Furthermore, in carrying out this reaction, it is generally preferred to react one mole of the compound of Formula III above with one mole of the compound of Formula IV above. However, if desired a molar excess of the compound of Formula III above or the compound of Formla IV above can be employed.

The acetylenic compound of Formula VII above can be converted to rhodoxanthin by partially hydrogenating the compound of Formula VII above at the triple bond to reduce all of the triple bonds contained therein to double bonds. The reduction of the compounds of Formula VII above to rhodoxanthin can be effected by

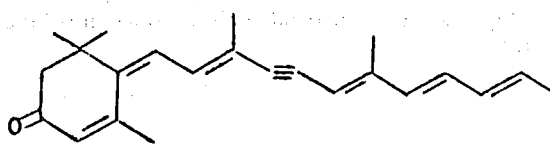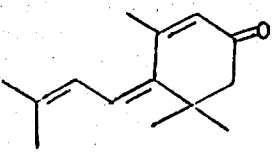

(VII)

This reaction is preferably carried out in the presence of a solvent, i.e., an organic solvent substantially inert to the reactants, such as a lower alkanol solvent, i.e., methanol, ethanol, etc., dimethylformamide, acetonitrile, or benzene. The preferred solvents are methanol and benzene. The reaction is conducted in the presence of a strong base, such as an alkali metal hydride, e.g., sodium hydride, potassium hydride, an alkali metal amide, e.g., sodium amide, an alkali metal lower alkoxide, preferably sodium ethoxide, or solution of an alkali metal hydroxide in a lower alkanol, e.g., KOH in methanol. Other strong bases which can be utilized include aryl or alkyl group I-A metallo organic compounds catalytic hydrogenation in the presence of a catalyst which selectively reduces only the triple bond (acetylene linkage) to a double bond. For example, compounds of Formula VII above can be catalytically hydrogenated, in an inert solvent such as ethyl acetate, toluene or petroleum ether, in the presence of a selective hydrogenation catalyst, e.g., a palladium-lead catalyst in the presence of quinoline, of the type disclosed in the publication Helvetica Chimica Acta, 35, 446 (1952).

The phosphonium salt of Formula III above can be synthesized from a compound of Formula I above by means of the following reaction scheme:

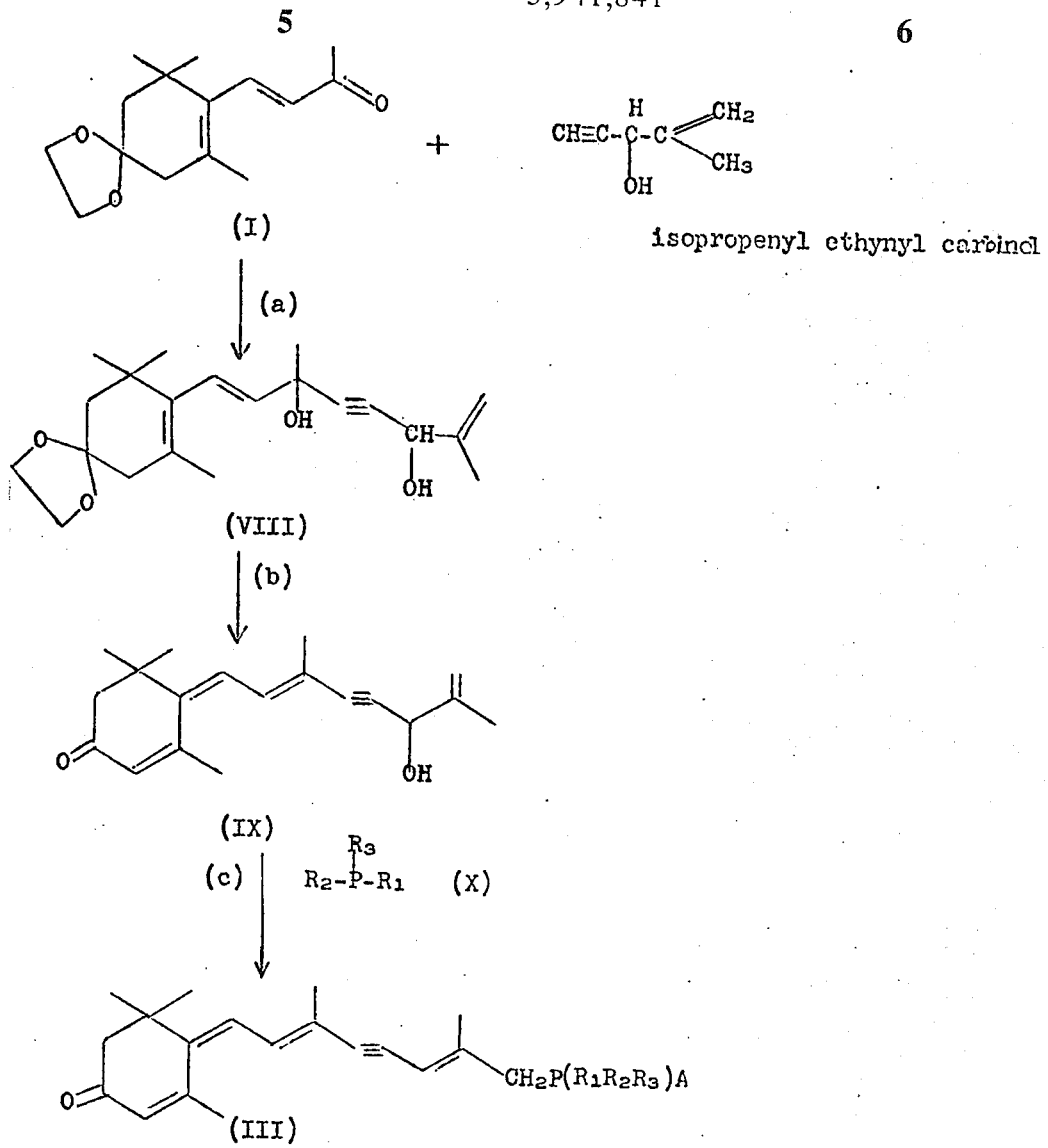

isopropenyl ethynyl carbinol wherein $R_1$, $R_2$, $R_3$ and A are as above.

The condensation reaction of the compound of Formula I above with isopropenyl ethynyl carbinol is carried out in an inert solvent in the presence of a Grignard reagent. Any conventional inert organic solvent can be utilized as the reaction medium in accordance with this invention. Included among the solvents suitable for the purpose of the present invention are hydrocarbons such as benzene, toluene, xylene, and the like; ethers such as tetrahydrofuran, diethyl, ether, dioxane, and the like, or any other suitable solvent. Any conventional Grignard reagent may be utilized in the condensation reaction of the compound of Formula I above with isopropenyl ethynyl carbinol. Typical Grignard reagents include lower alkyl metallic halides. Among the many Grignard reagents that can be utilized in accordance with this invention are included ethyl magnesium chloride, ethyl magnesium bromide, phenyl magnesium iodide, chlorophenyl lithium, etc. In carrying out the condensation reaction of step (a), temperature and pressure are not critical and the reaction can be carried out at room temperature and at atmospheric pressure. If desired, the reaction of step (a) can be carried out at reduced temperatures and/or reduced or elevated pressure. Generally, it is preferred to carry out the reaction step (a) at the reflux temperature of the solvent.

The compound of Formula VIII above is converted to the compound of Formula IX above by dehydration, due to the instability of the tertiary hydroxy group, and by hydrolysis. Any conventional dehydration and hydrolysis procedure can be utilized to hydrolyze and to remove the tertiary hydroxy group from the compound of Formula VIII to convert it into the compound of Formula IX above. This can be accomplished by treating the compound of formula VIII above with a dilute acid such as sulfuric acid, paratoluenesulfuric acid, hydrochloric acid, hydrobromic acid, etc. Generally, in utilizing an acid, no more than 10 parts by weight, preferably from about 0.1 to 7.0 parts by weight of the acid should be utilized, based upon the weight of the reaction medium. When treating a compound of formula VIII with dilute acid simultaneously with the dehydration the ketalized oxo group is hydrolyzed to an oxo group. If desired, the dehydration reaction can be carried out by heating the compound of Formula VIII in the presence of a water-binding agent. In such a case a separate hydrolysis step is required for converting the ketalized oxo group to an oxo group. Water-binding agents are meant to include such substances as have a marked tendency to add on water physically or in complex form, also in the presence of organic solvents. It is known to any worker in the art which agents are to be used in each particular case.

In step (c), the compound of Formula IX above is coverted into the compound of Formula III by means of reacting the compound of Formula IX above with a phosphine of Formula X above in the presence of a proton donor or with an acid addition salt of a phosphine of Formula X above. Proton donors which can be employed in the above process include inorganic acids, such as the hydrohalic acids (especially hydrochloric acid) or sulfuric acid. Moreover, all acids which form acid addition salts with phosphines of Formula X (e.g., strong organic acids such as benzenesulfonic acid or trichloroacetic acid) as well as those specifically named above, can be employed. When an acid addition salt of the phosphine of Formula X above is utilized, the acid used to form the acid addition salt can be any strong acid such as the mineral acids and the strong organic acids such as the sulfonic acids, e.g., benzene and toluenesulfonic acid, etc. The reaction of step (c) is carried out in the presence of an inert solvent, such as, for example, a lower alkanol such as methanol or ethanol. Generally, this reaction is carried out under substantially anhydrous conditions, that is, the reaction medium or solvent should not contain more than 10 percent by weight of water. In carrying out the reaction of step (c), temperature and pressure are not critical. Hence, the reaction of step (c) can be carried out at room temperature or elevated or reduced pressure. In this manner, a compound of Formula III above is formed.

The oxo aldehyde compound of Formula VI above is prepared from the compound of Formula I above by means of the following reaction scheme:

wherein $R_4$, $R_5$, and $R_6$ are lower alkyl groups.

The compound of Formula XI above is condensed with the compound of Formula I above in the presence of a Grignard agent to produce the compound of Formula XII. This Grignard condensation reaction as in step (d) is carried out in the same manner and utilizing the same general conditions as was utilized in the condensation reaction in step (a). Generally, this condensation reaction is carried out by condensing one mole of the compound of Formula XI with one mole of the compound of Formula I above in the presence of a Grignard agent such as those mentioned hereinbefore. This condensation reaction is carried out by utilizing an inert organic solvent as the reaction medium. The compound of Formula XII thus obtained is then hydrolyzed in an acid medium to produce the compound of Formula IV above. This hydrolysis proceeds with the simultaneous splitting off of alcohol and water from the molecule so as to convert the two terminal ether groups to an aldehyde group while forming an additional double bond within the compound of Formula XII above. Furthermore, the dioxo radical is converted to a keto group and the tertiary hydroxy group is removed from the molecule. This reaction step can suitably be carried out in the presence of a water-soluble, non-volatile organic or inorganic acid such as paratoluenesulfonic acid, acetic acid, propionic acid, oxalic acid, sulfuric acid, phosphoric acid, or a water-soluble acid salt such

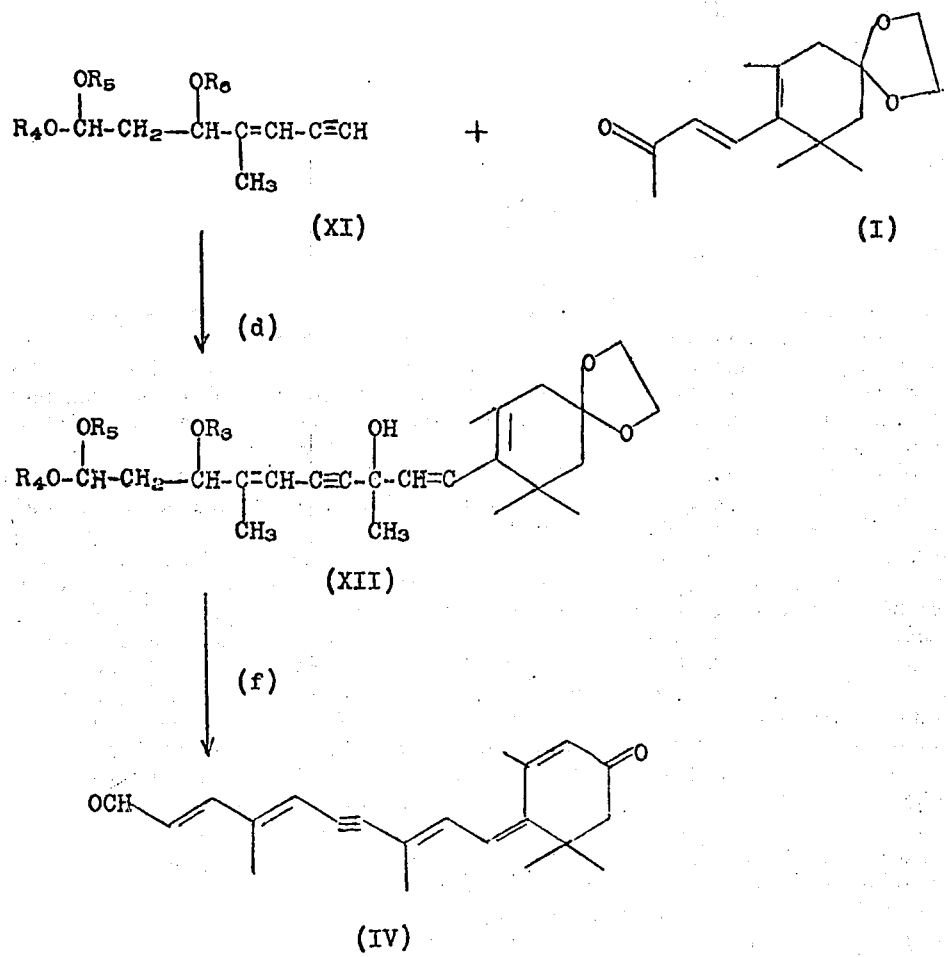

as zinc chloride. Acetic acid with the addition of a little water is preferred. The hydrolysis is conveniently carried out in the presence of an added sodium salt, preferably sodium acetate. The reaction is preferably carried out with exclusion of oxygen and the addition of an antioxidant, e.g., hydroquinone. The reaction is best carried out under conditions wherein the alcohol formed by the reaction distills off from the reaction mixture. A water-miscible solvent can be employed such as dioxane, tetrahydrofuran, ethylene glycol, dimethyl ether, etc., in order to obtain a homogeneous reaction mixture. Any conventional hydrolysis conditions can be utilized in carrying out this reaction. In carrying out this hydrolysis reaction, it is preferable to use elevated temperatures. However, this reaction will proceed at room temperature and the alcohol that formes during the reaction can be separated later by washing.

In accordance with another embodiment of this invention, rhodoxanthin can be directly synthesized by condensing one mole of a compound of Formula V above with one mole of a compound of Formula VI above. The conditions utilized in condensing the compound of Formula V above with the compound of Formula VI above are the same that are utilized in the condensation of the compound of Formula III above with that of Formula IV above to produce a compound of Formula VII.

The compound of Formula V above can be produced from the compound of Formula IX above by means of the following reaction scheme:

In the above scheme $R_1$, $R_2$, $R_3$ and A have the same meaning hereinbefore given.

In converting the compound of Formula IX above to the compound of Formula XIII above, the compound of Formula XIII above is selectively hydrogenated to reduce the triple bond contained therein to a double bond. This hydrogenation procedure can be carried out in the same manner as was described in connection with the hydrogenation of the compound of Formula VII above to rhodoxanthin.

The compound of Formula XIII above which is formed by the hydrogenation reaction in step (h) is converted to the compound of Formula V above by reaction with a phosphonium salt of Formula X above in the presence of a proton donor or with the acid addition salt of the phosphonium compound of Formula X above. This reaction is carried out in the same manner and utilizing the same conditions as in the conversion of the compound of Formula IX above to the compound of Formula III above in step (c).

The compound of Formula VI above is prepared from the compound of Formula IV above by selectively hydrogenating the triple bond in the compound of Formula IV above to a double bond. This selective hydrogenation can be carried out in the same manner outlined with regard to the conversion of the compound of Formula VII above to rhodoxanthin.

The ionone compound of Formula I above which is utilized to prepare the intermediates in accordance with this invention can be synthesized by the following reaction scheme:

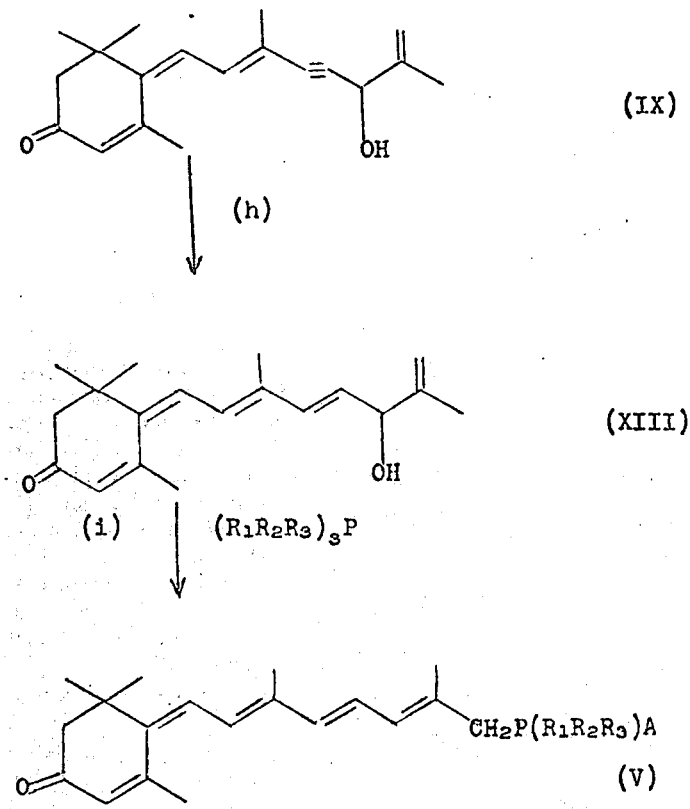

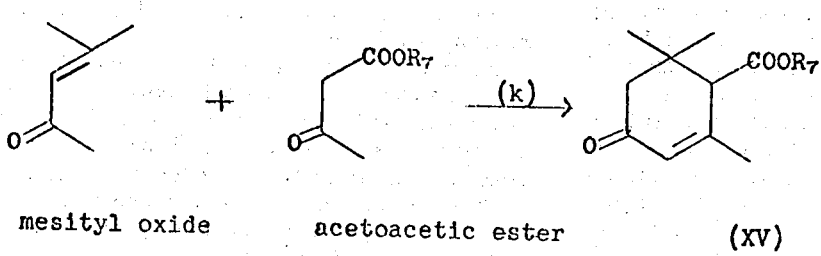

mesityl oxide    acetoacetic ester    (XV)

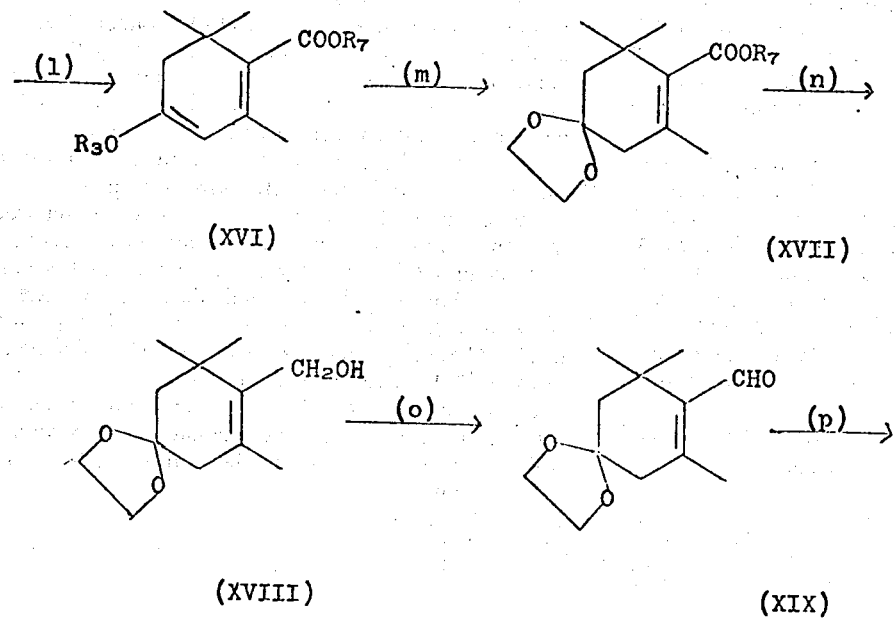

(XVI)      (XVII)

(XVIII)      (XIX)

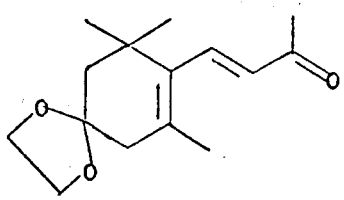

(I)

wherein $R_7$ and $R_8$ are lower alkyl groups.

The condensation, as in step (k), of mesityl oxide and acetoacetic acid ester to form the lower alkyl ester of 3,5,5-trimethyl-2-cyclohexen-1-one-4-carboxylic acid (Formula XV above) is carried out by condensing one mole of mesityl oxide with one mole of aceto acid ester at reflux temperature in the presence of an inert organic solvent utilizing an acid catalyst, such as an acid condensing agent. Any conventional inert organic solvents, preferably those which are immiscible with water, can be utilized in carrying out this reaction. Typical organic solvents which can be utilized in carrying out this reaction include chloroform, carbon tetrachloride, hydrocarbon solvents such as benzene, heptane, etc. In carrying out this reaction, any conventional acid catalyst can be utilized. The acid condensing agent or catalyst which can be utilized in accordance with this invention are preferably strong acids such as the mineral acids, Lewis acids, e.g., boron trifluoride, zinc chloride, etc., strongly acidic organic acids such as toluenesulfonic acid, oxalic acid, trichloroacetic acid, etc. In carrying out this condensation reaction, the reflux temperature of the solvent medium could be utilized. This temperature can vary from 50° C. to 150° C. depending upon the solvent utilized. The conversion of the ester compound of Formula XV above to the etherified carboxylic acid ester compound of Formula XVI above is carried out by treating the compound of Formula XV above with a lower alkyl triester of formic acid in the presence of an inorganic acid or mineral acid. This reaction is preferably carried out in an organic solvent. Any of the aforementioned solvents can be utilized in carrying out this reaction. Any of the conventional mineral acids such as sulfuric acid, hydrochloric acid, hydrobromic acid, phosphoric acid, etc., can be utilized in carrying out this reaction. Typical esters of formic acid which can be utilized in carrying out this reaction include triethylorthoformate, trimethylorthoformate, triisopropylorthoformate, etc. In carrying out this reaction, temperature and pressure are not critical and the conversion of the compounds of Formula XV above to the compounds of Formula XVI above can be effected at room temperature and at atmospheric pressure or at elevated or reduced temperatures and/or elevated or reduced pressure.

The ether compound of Formula XVI above is converted to the dioxycarboxylic acid ester of Formula XVII above by treating compounds of Formula XVI above with ethylene glycol at elevated temperatures in an inert organic solvent medium. Any of the conventional inorganic solvents such as the aformentioned solvents can be utilized in carrying out this reaction. This reaction is carried out by utilizing an acid catalyst such as any of the aforementioned acid catalysts or condensing agents. In carrying out this reaction, temperatures of above a temperature of about 60° should be utilized. The highest temperature which can be utilized in carrying out this reaction will depend upon the reflux temperature of the reaction medium. The ethylene glycol which is utilized in this reaction should be present so as to provide one mole of ethylene glycol per mole of the compound of Formula XVI above.

Upon treatment of the compound of Formula XVII above with an alkali metal aluminum hydride reducing agent such as lithium aluminum hydride, sodium aluminum hydride, etc., the ester radical on the compound of Formula XVII above is reduced to a hydroxy radical to produce the corresponding dioxyhydroxy compound of Formula XVIII above. The reduction with the alkali metal aluminum hydride reducing agent is preferably carried out under anhydrous conditions in the presence of an inert organic solvent such as any of the aforementioned organic solvents. The reaction is suitably carried out at room temperature. However, temperatures of from about −20° C. to about 80° C. can be utilized in carrying out this reaction.

The dioxyhydroxy compound of Formula XVIII above can be converted to the corresponding dioxyaldehyde compound of Formula XIX above by means of oxidation. Any conventional oxidizing technique can be utilized to oxidize the compounds of Formula XVIII above to the compounds of Formula XIX above. The dioxyaldehyde compound of Formula XIX above can be converted to the ionone compounds of Formula I above by means of condensing one mole of the compound of Formula XIX above with one mole of acetone as in step (p). This condensation reaction should be carried out in the presence of a strong base, preferably an alkali metal hydroxide such as potassium hydroxide, sodium hydroxide, sodium methoxide, lithium hydroxide, calcium hydroxide, etc. In carrying out the condensation reaction of step (p) temperature and pressure are not critical so that the reaction can be carried out at room temperature. However, if desired, elevated or reduced temperatures can be utilized as well as elevated or reduced pressures. This reaction is carried out in an organic solvent media, preferably acetone.

The following examples illustrate the invention. In the examples, the petroleum ether utilized boiled at a range of 60° C. to 80° C. All temperatures utilized in the following examples are in degrees centigrade.

Example 1

3,5,5-Trimethyl-2-Cyclohexen-1-on-4-Carboxylic Acid Methyl Ester

A mixture of 2.6 kg. of methyl acetoacetate, 2.75 kg. of mesityl oxide, 400 g. of zinc chloride, 2 l. of heptane, and 2 l. of benzene was refluxed for 5 days. The water formed during the reaction was azeotropically distilled off and collected in a separator. A brown oily product remained in the flask. The oily product was then washed with water, sodium bicarbonate solution, and again with water. The oil which remained after washing was dried over calcium chloride and the heptane-benzene solvent removed under vacuum. The remaining oil was distilled under high vacuum over a packed column. From the distillation there was obtained first a forecut of unreacted ethyl acetoacetate and mesityl oxide, a second fraction of isophorone by product and finally crude 3,5,5-trimethyl-2-cyclohexen-1-on-4-carboxylic acid methyl ester with a boiling range of 95°–104° at 0.4–0.6 mm.Hg. This crude material was utilized for all experiments without further purification. Pure 3,5,5-trimethyl-2-cyclohexen-1-on-4-carboxylic acid methyl ester was obtained by chromatographic separation on silica gel G (finely divided powdered Silica containing trace amounts of calcium sulfate), using petroleum ether and ethyl ether in a volume ratio of 7 to 3.

Example 2

7,9,9-Trimethyl-1,4-Dioxaspiro[4,5]dec-7-en-8-Carboxylic Acid Methyl Ester 800 g. of crude 3,5,5-trimethyl-2-cyclohexen-1-on-4-carboxylic acid methyl ester and 720 g. of triethyl orthoformate were mixed with 1.5 l of anhydrous ethanol containing 4 ml. of sulfuric acid. After standing for 4 hours at room temperature, the dark blue solution was poured onto petroleum ether over a sodium bicarbonate solution. The ether layer was washed twice with water, dried over sodium sulfate and concentrated by removing all of the ether solvent. The resulting dark residue was distilled over a vigreux column under high vacuum to yield 2,6,6-trimethyl-4-ethoxy-1,3-cyclohexadien-1-carboxylic acid methyl ester.

670 g. of crude 2,6,6-trimethyl-4-ethoxy-1,3-cyclohexadien-1-carboxylic acid methyl ester and 185 g. of ethylene glycol were heated in 3 l. of benzene in the presence of 3 g. of p-toluene sulfonic acid. The reaction was stopped after 1.5 l. of benzene had distilled over. The cold solution was washed with sodium bicarbonate solution and water, dried, and evaporated. The remaining oil was dissolved in 1 l. of petroleum ether and crystallized at −10°. A yield of 320 g. (m.p. 67°–69°) was obtained after recrystallization from petroleum ether. This product was identified as 7,9,9-trimethyl-1,4-dioxaspiro[4,5]dec-7-on-8-carboxylic acid methyl ester.

Example 3

7,9,9-Trimethyl-1,4-Dioxaspiro [4,5]dec-7-en-8-Methanol

A solution of 300 g. of 7,9,9-trimethyl-1,4-dioxaspiro[4,5]dec-7-en-8-carboxylic acid methyl ester in 1 l. of ether was slowly added to a stirred suspension of 50 g. of lithium aluminum hydride in 1 l. of ethyl ether. During the addition, which required 1 hour, the temperature was kept between 15° and 20°. It was then allowed to climb to room temperature, and stirring under nitrogen was continued for 4 hours. After quenching the reaction by slow addition of 250 ml. of water at 5°–15°, the inorganic material was filtered by suction. The filtrate was dried over sodium sulfate and concentrated to yield a viscous oil which solidified on refrigeration. Recrystallization from ethyl ether-petroleum ether gave pure material. The material was analyzed as 7,9,9-trimethyl-1,4-dioxaspiro[4,5]dec-7-en-8-methanol.

Example 4

7,9,9-Trimethyl-1,4-Dioxaspiro[4,5]dec-7-en-8-Carboxaldehyde 3 kg. of maganese dioxide was added in four portions over a period of 2 days to a solution of 150 g. of crystalline 7,9,9-trimethyl-1,4-dioxaspiro[4,5]dec-7-en-8-methanol in 3 l. of methylene chloride. After the mixture was stirred under nitrogen for an additional day, the oxidation was complete according to a determination by thin layer chromatography. Filtration and evaporation of the solvent yielded the crude product which was used for the next step without further purification. A small portion of this product was purified by vacuum distillation. This product was identified as 7,9,9-trimethyl-1,4-dioxaspiro[4,5]dec-7-en-8-carboxaldehyde.

Example 5

3-Ethylenedioxy-β-Ionone

A mixture of 120 g. of crude 7,9,9-trimethyl-1,4-dioxaspiro[4,5]dec-7-en-8-carboxaldehyde, 500 ml. of acetone, and 60 ml. of 10% aqueous solution of potassium hydroxide was refluxed under nitrogen for 16 hours. Most of the solvent was removed under vacuum and the residue was diluted with water and extracted with petroleum ether leaving an oil layer. The oil layer was washed neutral with water, dried over sodium sulfate and concentrated. The residue was distilled under reduced pressure over a vigreux column. The fraction boiling between 115° and 140° at 0.3 to 0.7 mm Hg. crystallized from petroleum ether at −10° to −20°. Recrystallization from petroleum ether yielded 60 g. of the 3-ethylenedioxy-β-ionone.

Example 6

2,6-Dimethyl-8-(4-Oxo-2,6,6-Trimethyl-2-Cyclohexenylidene)-1,6-Octadien-4-yn-3-ol 9.6 g. of isopropenyl-ethynyl-carbinol was dropped into a suspension of ethyl magnesium bromide in 200 ml. of ether (prepared from 6.1 g. of magnesium and 27 g. of ethyl bromide) and refluxed for 45 min. 20 g. of 3-ethylenedioxy-β-ionone in 100 ml. of ethyl ether was then added to the mixture, which was cooled with ice water. After stirring for 1 hour at room temperature, the reaction mixture was quenched with water forming a magnesium hydroxide precipitate. The precipitate dissolved in the reaction media by addition of 5% sulfuric acid. Two layers were formed, an aqueous layer and an ether layer which contained the product. The ether layer was separated from the aqueous layer. The separated ether layer was washed with water, dried and concentrated by removing the solvent to yield the crude compound of formula VIII above.

This crude compound of formula VIII above was refluxed for 2 hours, with stirring, in 100 ml. of methylene chloride and 20 ml. of 5% aqueous sulfuric acid. The methylene chloride solution was washed neutral, dried over sodium sulfate and concentrated by distilling off the solvent. Crude 2,6-dimethyl-8-(4-oxo-2,6,6-trimethyl-2-cyclohexenylidene)-1,6-octadien-4-yn-3-ol was obtained. This crude product was purified by chromatography on 300 g. of silica gel G using petroleum etherethyl ether in volume ratio of 1 to 1.

Example 7

2,6-Dimethyl-8-(4-Oxo-2,6,6-Trimethyl-2-Cyclohexenylidene)-2,6-Octadien-4-yne Triphenylphosphonium Bromide 9 g. of triphenylphosphonium bromide was added to a solution which consisted of 5 g. of purified 2,6-dimethyl-8-(4-oxo-2,6,6-trimethyl-2-cyclohexenylidene)-1,6-octadien-4-yn-3-ol and 200 cc. of benzene. After standing at room temperature for 16 hours, the solution was washed three times with water, dried over sodium sulfate, and concentrated to remove solvent. The residue was dispersed in ethyl acetate to remove triphenylphosphine. The separated solid crystallized partially from ethyl acetatemethanol to yield crystalline material. This material was identified as 2,6-dimethyl-8-(4-oxo-2,6,6-trimethyl-2-cyclohexenylidene)-2,6-octadien-4-yne triphenylphosphonium bromide.

Example 8

4,8-Dimethyl-10-(4-Oxo-2,6,6-Trimethyl-2-Cyclohexenylidene)-2,4,8-Decatrien-6-ynal 24 g. of 4-methyl-1,1,3-triethoxy-4-hepten-6-yne was dropped into a suspension of ethyl magnesium bromide prepared from 2.7 g. of magnesium and 14 g. of ethyl bromide in 50 ml. of ethyl ether. After 30 min. of reflux, 20 g. of 3-ethylenedioxy-β-ionone in 100 ml. of ether was added at −5°. The reaction was then stirred for 2 hours at room temperature and quenched with water forming two layers, i.e., a water and an ether layer which contained compound of formula XII above. The decanted ether layer was dried and concentrated to remove ethyl ether. The compound XII which formed a residue was heated on the steam bath for 3 hours with 250 ml. of acetic acid, 30 ml. of water and 40 g. of sodium acetate forming a dark solution. The dark solution was diluted with water and extracted with an ethyl ether-petroleum ether mixture. The extracts were washed neutral with sodium carbonate and water, dried and concentrated to yield a dark residue which partially crystallized on refrigeration. This was then purified by chromatography on 400 g. of silica gel G with the solvent system benzene ethyl ether in a volume ratio of 3:2. The product was identified as 4,8-dimethyl-10-(4-oxo-2,6,6-trimethyl-2-cyclohexenylidene)-2,4,8-decatrien-6-ynal.

Example 9

10,11-10',11'-Bis-Dehydro-Rhodoxanthin
[trans-3,7,12,16-tetramethyl-1,18-bis(2,6,6-trimethyl-4-oxo-2-cyclohexen-1-ylidene)
2,6,8,10,12,16-octadecahexaene-4,14-diyne]

1 g. of sodium methoxide was added slowly to a stirred solution of 2.6 g. of 2,6-dimethyl-8-(4-oxo-2,6,6-trimethyl-2-cyclohexenylidene)-2,6-octadien-4-yne triphenylphosphonium bromide and 1.2 g. of 4,8-dimethyl-10-(4-oxo-2,6,6-trimethyl-2-cyclohexenylidene)-2,4,8-decatrien-6-ynal in 20 ml. of methanol. The reaction was stirred for 6 hours at 0° to 5° and a precipitate formed. The precipitated carotenoid was filtered and recrystallized from benzene-methanol to yield red needles. This compound was identified as 10,11-10',11'-bis-dehydro-rhodoxanthin.

Example 10

4-Cis-2,6-Dimethyl-8-(4-Oxo-2,6,6-Trimethyl-2-Cyclohexenylidene)-1,4,6-Octatrien-3-ol 6.5 g. of purified 2,6-dimethyl-8-(4-oxo-2,6,6-trimethyl-2-cyclohexenylidene)-1,6-octadien-4-yn-3-ol was hydrogenated with 1 g. of Lindlar catalyst (a palladium-clacium carbonate catalyst deactivated by the addition of lead and quinoline) in benzene. 700 ml. of hydrogen was consumed within 4 hours. After this period, the catalyst was removed from the solution and the solution was washed with water, then dried and evaporated under reduced pressure. The product was purified by chromatography on 200 g. of silica gel G using petroleum ether and ethyl ether solvent in a volume ratio of 1 to 3. The material was identified as 4-cis-2,6-dimethyl-8-(4-oxo-2,6,6-trimethyl-2-cyclohexenylidene)-1,4,6-octatrien-3-ol).

Example 11

2,6-Dimethyl-8-(4-Oxo-2,6,6-Trimethyl-2-Cyclohexenylidene)-2,6,8-Octatrien Triphenylphosphonium Bromide 4 g. of pure 4-cis-2,6-dimethyl-8-(4-oxo-2,6,6-trimethyl-2-cyclohexenylidene)-1,4,6-octatrien-3-ol and 7 g. of triphenylphosphonium bromide were dissolved in 200 cc. of methylene chloride and allowed to react for 16 hours. The solution was then washed 4 times with water, dried and concentrated to remove solvent. The residue was dispersed in 200 cc. of ethyl acetate, and the insoluble material was filtered off and dissolved in an ethyl acetate-methanol mixture where it crystallized partially. This product was identified as 2,6-dimethyl-8-(4-oxo-2,6,6-trimethyl-2-cyclohexenylidene)-2,6,8-octatrien triphenylphosphonium bromide.

Example 12

4,8-Dimethyl-10-(4-Oxo-2,6,6-Trimethyl-2-Cyclohexenylidene)-2,4,6,8-Decatetraenal 2 g. of pure 4,8-dimethyl-10-(4-oxo-2,6,6-trimethyl-2-cyclohexenylidene)-2,4,8-decatrien-6-ynal in 50 ml. of benzene was hydrogenated in the presence of 0.5 g. of Lindlar catalyst and 0.5 ml. of a 1% solution of quinoline in acetone. After consumption of 240 ml. of hydrogen, which took place within 2½ hours, the suspension was filtered and concentrated. The residue crystallized only partially after chromatography on 200 g. of silica gel G with benzene ethyl ether in a volume ratio of 3:2.

Example 13

Rhodoxanthin 0.5 g. of 10,11,10',11'-bis-dehydro-rhodoxanthin in 50 ml. of benzene was hydrogenated in the presence of 100 mg. of Lindlar catalyst and 0.1 ml. of a 1% solution of quinoline in acetone. After 65 ml. of hydrogen had been consumed (within 2 hours), the filtered solution was concentrated. The residue was placed in a sealed tube with 2.5 ml. of benzene and 5 ml. of heptane and heated on the steam bath for 24 hours. During this isomerization, rhodoxanthin crystallized out in dark violet crystals. The rhodoxanthin was recrystallized from benzeneheptane mixture.

0.2 g. of 4,8-dimethyl-10-(4-oxo-2,6,6-trimethyl-2-cyclohexenylidene)-2,4,6,8-decatetraenal and 0.35 g. of 2,6-dimethyl-8-(4-oxo-2,6,6-trimethyl-2-cyclohexenylidene)-2,4,6-octatrien triphenylphosphonium bromide were dissolved in 6 ml. of methanol and treated with 0.2 g. of sodium methoxide at 0° for 4 hours. The precipitated dark violet solid was collected and recrystallized from benzene methanol to yield rhodoxanthin.

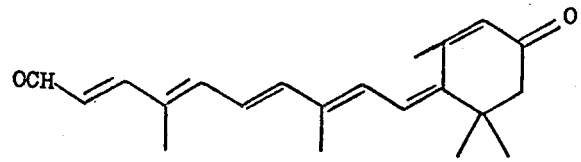

We claim:
1. A compound of the formula